United States Patent
Reddy et al.

(10) Patent No.: US 8,519,197 B2
(45) Date of Patent: Aug. 27, 2013

(54) SYNTHESIS OF MAGNOLOL AND ITS ANALOGUE COMPOUNDS

(75) Inventors: Basi V. Subba Reddy, Nacharam (IN); Jhillu S. Yadav, Hyderabad (IN); Ravi Subramanyam, Mumbai (IN)

(73) Assignees: Colgate-Palmolive Company, New York, NY (US); Indian Institute of Chemical Technology (IN)

( * ) Notice: Subject to any disclaimer, the term of this patent is extended or adjusted under 35 U.S.C. 154(b) by 0 days.

(21) Appl. No.: 13/577,627

(22) PCT Filed: Feb. 25, 2010

(86) PCT No.: PCT/US2010/025378
§ 371 (c)(1),
(2), (4) Date: Aug. 7, 2012

(87) PCT Pub. No.: WO2011/106003
PCT Pub. Date: Sep. 1, 2011

(65) Prior Publication Data
US 2012/0302647 A1    Nov. 29, 2012

(51) Int. Cl.
*C07C 39/12* (2006.01)

(52) U.S. Cl.
USPC ........................................... 568/730

(58) Field of Classification Search
USPC ........................................... 568/730
See application file for complete search history.

(56) References Cited

U.S. PATENT DOCUMENTS

| | | |
|---|---|---|
| 6,544,409 B2 | 4/2003 | DeSouza |
| 2006/0140885 A1 | 6/2006 | Gaffar et al. |

OTHER PUBLICATIONS

Agharahimi et al., "Synthesis of (−)-Monoterpenylmagnolol and Magnolol," Journal of Organic Chemistry (1995), vol. 60, pp. 1856-1863.
Gu et al., "Enantioselective syntheses of (S)- and (R)-8,9-dihydroxydihydromagnolol," Tetrahedron: Asymmetry 9 (1998), pp. 1377-1380.
Huang et al., "Synthesis and Ocular Hypotensive Activity of Magnolol," The Chinese Pharmaceutical Journal (2006), 58, 115-122.
Lee et al., "Anti-inflammatory and Neuroprotective Effects of Magnolol in Chemical Hypoxia in Rat Cultured Cortical Cells in Hypoglycemic Media," Chinese Journal of Physiology (2000), 43(2):61-67.
Runeberg, "Phenol Dehydrogenations," Acta Chemica Scandinavica (1958), 12, pp. 188-192.

*Primary Examiner* — Jafar Parsa
(74) *Attorney, Agent, or Firm* — Howard C. Lee

(57) ABSTRACT

A method is described for producing magnolol, or a derivative or analogue thereof. The method includes obtaining MOM ether of 5,5'-diallylbiphenyl-2,2'-diol or a derivative or analogue thereof and subsequently converting the MOM ether of 5,5'-diallylbiphenyl-2,2'-diol into magnolol or a derivative or analogue thereof.

20 Claims, No Drawings

SYNTHESIS OF MAGNOLOL AND ITS ANALOGUE COMPOUNDS

FIELD OF THE INVENTION

The embodiments of the invention relate to a method of producing magnolol or its analogue compounds. The embodiments also relate to a pharmaceutically or orally acceptable composition comprising magnolol or its analogue compounds prepared according to the methods described herein.

BACKGROUND OF THE INVENTION

Magnolol (5,5'-diallylbiphenyl-2,2'-diol or 5,5'-dially-2,2'-bisphenol), together with honokiol, are the major ingredients found in magnolia extracts. It is well recognized in the art that magnolia extracts have found, among other things, applications in compositions to treat bacteria and/or inflammation related oral diseases. See, e.g., U.S. Pat. No. 6,544.409, and U.S. patent application publication No. U.S. 2006/0,140,885, the disclosures of which are incorporated by reference herein in their entireties.

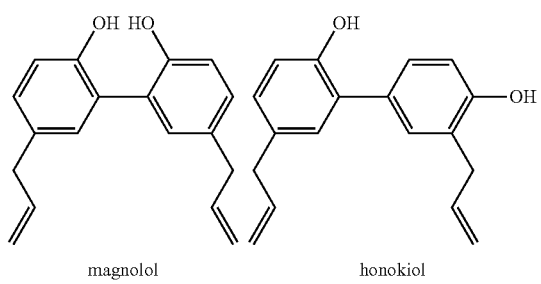

Studies have further revealed that magnolol, as an independent active substance, also plays an important role in other pharmacological processes besides its anti-bacterial and anti-inflammatory activities. For example, magnolol has been shown to exhibit a beneficial capability of protecting the myocardium against infarction and reperfusion injury. It has also been shown that magnolol protects neurons against chemical hypoxia by KCN in cortical neuron-astrocyte mixed cultures. More recently, it is reported, that magnolol possesses an antioxidant activity 1000 times greater than α-tocopherol, implicating magnolol's great potential in food and pharmaceutical applications. All these divergent uses reveal that there is a great need for high quality and affordable magnolol. See Wen-Hsin Huang et al., *The Chinese Pharmaceutical Journal*, 2006, 58, 115-122; Min-Min Lee et al. *Chinese Journal of Physiology*, 2000, 43, 61-67.

Currently, there are several synthetic methods of producing magnolol reported in the art, one of which is described in a paper by J. Runeberg, *Acta Chem Scand*, 1958, 12, 188-192, wherein the key reactant, methyl ether of 5,5'-dibromo-2,2'-bisphenol was reacted with allyl bromide in tetrahydrofuran (THF) in the presence of ethylmagnesium bromide to obtain methyl ether of 5.5'-diallylbiphenyl-2,2-diol as shown below:

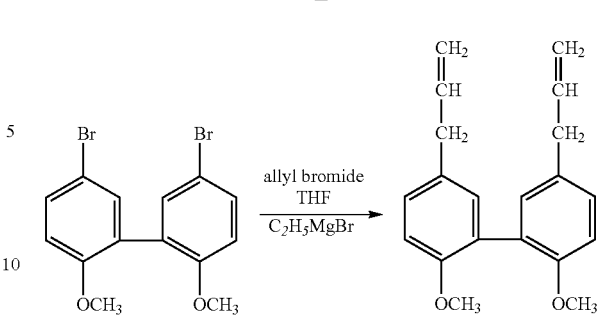

This reaction requires refluxing conditions, and provides a low yield of the desired product. Furthermore, the subsequent step of removing the methyl group of methyl ether of 5,5'-diallylbiphenyl-2,2'-diol to obtain magnolol requires even higher temperature, and the reaction mixture is difficult to separate and purify, thereby resulting in a low yield of magnolol.

Other reported synthetic methods of producing magnolol in the art also suffer similar problems such as low yields, difficulty in purification, the high cost of synthesis, and/or not practical or compatible for industrial scale. See, e.g., Wen-Hsin Huang et al., *The Chinese Pharmaceutical Journal*, 2006, 58, 115-122; and Wenxin On et al., *Tetrahedron: Asymmetry*, 1998, 9, 1377-1380. Therefore, there exists a practical need in the art to develop a synthetic method to produce high quality and affordable magnolol, as well as derivatives and analogues thereof.

SUMMARY OF THE INVENTION

In one embodiment, the invention encompasses a method of producing magnolol (5,5'-diallylbiphenyl-2,2'-diol) or its analogue compounds comprising reacting 2,2'-bisphenol with bromine at room temperature in an organic solvent to obtain 5,5'-dibromo-2,2'-bisphenol, subsequently protecting the two hydroxyl groups of 5,5'-dibromo-2,2'-bisphenol with methoxymethylchloride (MOM-Cl) in an organic solvent in the presence of an organic base to obtain MOM ether of 5,5'-dibromo-2,2'-bisphenol, and further reacting the MOM ether of 5,5'-dibromo-2,2'-bisphenol with a substituted or unsubstituted allyl bromide in an organic solvent with magnesium and ethyl bromide to effect the coupling and thus obtain MOM ether of 5,5'-diallylbiphenyl-2,2'-diol or a derivative or analogue thereof, and converting the MOM ether of 5,5'-diallylbiphenyl-2,2'-diol or a derivative or analogue thereof with a suitable agent to obtain magnolol or a derivative or analogue thereof.

In another embodiment, the invention encompasses a method of producing MOM ether of 5,5'-diallylbiphenyl-2,2'-diol comprising reacting 2,2'-bisphenol with bromine at room temperature in an organic, solvent to obtain 5,5'-dibromo-2,2'-bisphenol, subsequently protecting the two hydroxyl groups of 5,5'-dibromo-2,2'-bisphenol with methoxymethylchloride (MOM-Cl) in an organic solvent in the presence of an organic base to obtain MOM ether of 5,5'-dibromo-2,2'-bisphenol, and further reacting the MOM ether of 5,5'-dibromo-2,2'-bisphenol with as substituted or unsubstituted allyl bromide in an organic solvent with magnesium and ethyl bromide to effect the coupling and thus obtain MOM ether of 5,5'-diallylbiphenyl-2,2'-diol or its analogue compounds.

In yet another embodiment, the invention encompasses an intermediate compound of MOM ether of 5,5'--diallylbiphenyl-2,2'-diol, or a derivative or analogue thereof.

In yet a further embodiment, the invention encompasses a method for producing magnolol (5,5'-diallylbiphenyl-2,2'-diol) or a derivative or analogue thereof comprising obtaining an intermediate compound of MOM ether of 5,5'-diallylbiphenyl-2,2'-diol or a derivative or analogue thereof, and converting the MOM ether of 5,5'-diallylbiphenyl-2,2'-diol or a derivative or analogue thereof with a suitable agent to obtain magnolol or a derivative or analogue thereof.

In yet a further embodiment, the invention encompasses a method for producing magnolol (5,5'-diallylbiphenyl-2,2'-diol) or a derivative or analogue thereof comprising converting the MOM ether of 5,5'-diallylbiphenyl-2,2'-diol or a derivative or analogue thereof with a suitable agent to obtain magnolol or a derivative or analogue thereof.

In another embodiment, the invention encompasses a composition comprising an orally or pharmaceutically acceptable carrier, and an effective amount of magnolol or a derivative or analogue thereof prepared according to any of the methods described above.

DETAILED DESCRIPTION

The following definitions and non-limiting guidelines must be considered in reviewing the description of this invention set forth herein. The headings (such as "Background" and "Summary,") and sub-headings (such as "Compositions" and "Methods') used herein are intended only for general organization of topics within the disclosure of the invention, and are not intended to limit the disclosure of the invention or any aspect thereof in particular, subject matter disclosed in the "Background" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of as material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have an relevance to the patentability of the invention disclosed herein. Any discussion of the content of references cited in the Introduction is intended merely to provide a general summary of assertions made by the authors of the references, and does not constitute an admission as to the accuracy of the content of such references.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material. The recitation of a specific value herein, whether referring to respective amounts of components, or other features of the embodiments, is intended, to denote that value, plus or minus a degree of variability to account for errors in measurements. For example, an amount of 10% may include 9.5% or 10.5%, given the degree of error in measurement that will be appreciated and understood by those having ordinary skill in the art.

As used herein, the term "alkyl" means a linear or branched hydrocarbon chain with preferably between 1 and 10 carbon atoms. Examples of such alkyl groups include methyl, ethyl, propyl, isopropyl, butyl, isobutyl, t-butyl and suitable isomers of pentyl and hexyl, wherein the methyl group is preferred.

As used herein, the term "substituted or unsubstituted phenyl" describes a phenyl group whose phenyl ring is substituted if necessary one or more times. Further, the term "substituted" means that any one or more hydrogens on the designated atom is replaced with a selection from the indicated group, provided that the designated atom's normal valency is not exceeded, and that the substitution results in a stable compound.

As used herein, the term "comprising" means that other steps and other components that do not affect the end result may be utilized. The term "comprising" encompasses the expressions "consisting of," and "consisting, essentially of," The use of singular identifiers such as "the," "a," or "an" is not intended to be limiting solely to the use of a single component, but may include multiple components.

As used herein the term "room temperature" means the ambient temperature of an typical laboratory, which is usually about that of Standard Temperature and Pressure (STP). As used herein, a "purified" or "isolated" compound means the compound has been separated from the reaction mixture in which it was formed.

As used herein the term "increased pressure" refers to a pressure above 1 atmosphere as is commonly understood by one of skill in the art. Conversely, as used herein, the term "reduced pressure" means a pressure of below 1 atmosphere as commonly understood by one of skill in the art.

As used herein, the expressions "carrier" or "orally acceptable carrier" as used throughout this description denote any safe and effective materials for use herein. Such materials include, water, solvents, etc., that may contain a humecant such as glycerine, sorbitol, xylitol and the like. The carrier or orally acceptable carrier also may include additional components that are generally acceptable to a person skilled in the art.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof.

Examples of pharmaceutically acceptable salts include, but are not limited to, mineral or organic acid salts of basic residues such as amines, alkali or organic salts of acidic residues such as carboxylic acids, and the like.

As used herein, the term "effective amount" refers to an amount of a compound, or a combination of compounds, of the present invention effective when administered alone or in combination as an active ingredient.

The present invention provides a chemical synthetic sequence that is cost effective, has an easy work-up and purification methodology, and has scale-up compatability for the production of the active substance magnolol and derivatives or analogues thereof. The chemical synthetic sequence is easily reproducible on a large scale through simple and high-yield synthetic steps that lead to high-quality final products. The embodiments of the invention encompass a method of producing a compound of formula (I)

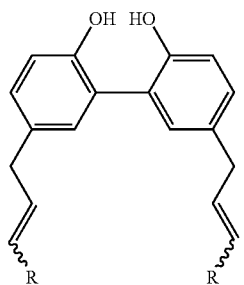

I wherein R represents H, alkyl, a substituted or unsubstituted phenyl group; or its pharmaceutically or orally acceptable salts. Accordingly, derivatives and analogues of magnolol include those in which R is not H. The method preferably comprises:

(a) reacting a compound of formula (II)

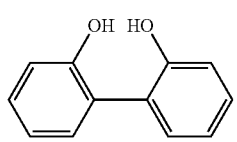

II with bromine in an organic solvent to obtain a compound of formula (III)

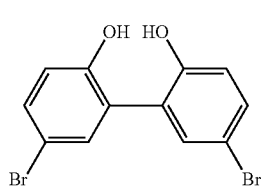

III (b) reacting the compound of formula III with MOM-Cl in an organic solvent in the presence of an organic base to produce a compound of formula (IV)

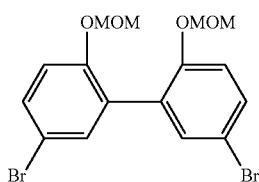

IV (c) reacting the compound of formula IV with R—CH=CH—CH$_2$—Br, wherein R is defined as above, in an organic solvent with magnesium and ethyl bromide to effect the coupling for an efficient amount of time to obtain a compound of formula V

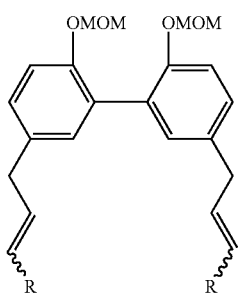

V (d) converting the compound of formula V with a suitable agent in an organic solvent to obtain a compound of formula I (e) optionally, converting the compound of formula I to its pharmaceutically or orally acceptable salts.

In one preferred embodiment, the invention encompasses as method of producing magnolol wherein R is hydrogen, or a derivative or analogue of magnolol wherein R is methyl or a phenyl. More preferably, the invention encompasses a method of producing magnolol wherein R is hydrogen.

In another embodiment, the invention encompasses a method of producing magnolol or a derivative or analogue thereof, wherein the first process includes reacting 2,2'-bisphenol with bromine at room temperature in an organic solvent selected from the group consisting of chloroform dichloromethane, dichloroethane, dimethylsulfoxide, dimethylformamide, acetonitrile, tetrahydrofuran, diethylether, hexane, acetone, methanol, ethanol, benzene, toluene. More preferable, the organic solvent is selected from the group consisting of chloroform, dichloromethane, tetrahydrofuran, methanol.

In yet another embodiment, the invention encompasses as method of producing magnolol or a derivative or analogue thereof, wherein step of protecting the two hydroxyl groups of 5,5'-dibromo-2,2'-bisphenol with methoxymethylchloride (MOM-Cl) in an organic solvent in the presence of an organic base includes using an organic base selected from the group consisting of triethylamine, diisopropylethylamine, pyridine, piperidine, lutidine, imidazole. More preferably, the organic base is selected from the group consisting of diisopropylethylamine, pyridine, piperidine and lutidine.

In yet a further embodiment, the invention encompasses as method of producing magnolol or a derivative or analogue thereof, wherein the suitable agent used to remove the MOM group is selected from the group consisting of boron halides, trimethylsilane iodide, and trimethylsilane chloride (TMS-Cl). More preferably, the agent is trimethylsilane chloride (TMS-Cl). Those skilled in the art are capable of determining a suitable agent capable of removing the MOM group (or deprotecting the MOM-containing derivative), using the guidelines provided herein.

The reaction may be carried out for a period of time sufficient to obtain the desired product. A "sufficient" amount of time depends in part on the desired extent of reaction and the reaction conditions, such as temperature. One of ordinary skill in the art can easily monitor the reaction to determine when a sufficient amount of time has transpired. The preferred amount of time is generally about 30 minutes to about 48 hours, preferably about 24 hours.

A preferred embodiment of the invention encompasses a method of producing magnolol (5,5'-diallylbiphenyl-2,2'-diol) or a derivative or analogue thereof comprising reacting 2,2'-bisphenol with bromine in an organic solvent such as chloroform to obtain 5,5'-dibromo-2,2'-bisphenol, subsequently protecting the two hydroxyl groups of 5,5'-dibromo-2,2'-bisphenol with methoxymethylchloride (MOM-Cl) in an organic solvent such as dichloromethane in the presence of an organic base such as diisopropylethylamine to obtain MOM ether of 5,5'-dibromo-2,2'-bisphenol, and further reacting the MOM ether of 5,5'-dibromo-2,2'-bisphenol with a substituted or unsubstituted allyl bromide in an organic solvent such as tetrahydrofuran with magnesium and ethyl bromide to effect the coupling and to obtain MOM ether of 5,5'-diallylbiphenyl-2,2'-diol or a derivative or analogue thereof (depending on whether the allyl bromide is substituted with other than hydrogen), and converting the MOM ether of 5,5'-diallylbiphenyl-2,2'-diol or its analogue compounds with a suitable deprotecting agent such as trimethylsilane chloride (TMS-Cl) in an organic solvent such as methanol to obtain magnolol or a derivative or analogue thereof. Magnolol or a derivative or analogue thereof can be optionally converted to their orally or pharmaceutically acceptable salts by a person having ordinary skill in the art.

In another embodiment, the invention encompasses a method of producing magnolol comprising reacting 2,2'-bisphenol with bromine in chloroform to obtain 5,5'-dibromo-2,2'-bisphenol, subsequently protecting the two hydroxyl groups of 5,5'-dibromo-2,2'-bisphenol with methoxymethylchloride (MOM-Cl) in dichloromethane in the presence of diisopropylethylamine to obtain MOM ether of 5,5'-dibromo-2,2'-bisphenol, further reacting, the MOM ether of 5,5'-dibromo-2,2'-bisphenol with allyl bromide in tetrahydrofuran with magnesium and ethyl bromide to effect the coupling, and to obtain MOM ether of 5,5'-diallylbiphenyl-2,2'-diol, and converting the MOM ether of 5,5'-diallylbiphenyl-2,2'-diol with trimethylsilane chloride (TMS-Cl) in methanol to obtain magnolol. Magnolol can optionally be converted, to its orally or pharmaceutically acceptable salts by a person having ordinary skill in the art.

In yet another embodiment, the invention encompasses a method of producing MOM ether of 5,5'-diallylbiphenyl-2, 2'-diol or a derivative or analogue thereof comprising reacting, 2,2'-bisphenol with bromine at room temperature in an organic solvent such as chloroform to obtain 5,5'-dibromo-2, 2'-bisphenol, subsequently protecting the two hydroxyl groups of 5,5'-dibromo-2,2'-bisphenol with methoxymethylchloride (MOM-Cl) in an organic solvent such as dichloromethane in the presence of an organic base such as diisopropylethylamine to obtain MOM ether of 5,5'-dibromo-2,2'-bisphenol, and further reacting the MOM ether of 5,5'-dibromo-2,2'-bisphenol with a substituted or unsubstituted allyl bromide in an organic solvent such as tetrahydrofuran with magnesium and ethyl bromide to effect the coupling and to obtain MOM ether of 5,5'-diallylbiphenyl-2,2'-diol, or a derivative or analogue thereof.

In a further embodiment, the invention encompasses a method of producing MOM ether of 5,5'-diallylbiphenyl-2, 2'-diol comprising reacting 2,2'-bisphenol with bromine at room temperature in chloroform to obtain 5,5'-dibromo-2,2'-bisphenol, and subsequently protecting the two hydroxyl groups of 5,5'-dibromo-2,2'-bisphenol with methoxymethylchloride (MOM-Cl) in dichloromethane in the presence of diisopropylethylamine to obtain MOM ether of 5,5'-dibromo-2,2'-bisphenol, and further reacting the MOM ether of 5,5'-dibromo-2,2'-bisphenol with allyl bromide in tetrahydrofuran through the involvement of magnesium turnings and ethyl bromide to obtain MOM ether of 5,5'-diallylbiphenyl-2,2'-diol.

In yet another embodiment, the invention encompasses a method of producing magnolol (5,5'-diallylbiphenyl-2,2'-diol) or a derivative or analogue thereof comprising obtaining MOM ether of 5,5'-diallylbiphenyl-2,2'-diol or a derivative or analogue thereof and converting the MOM ether of 5,5'-diallylbiphenyl-2,2'-diol or a derivative or analogue thereof to magnolol or a derivative or analogue thereof.

In yet another embodiment, the invention encompasses a method of producing magnolol comprising obtaining MOM ether of 5,5'-diallylbiphenyl-2,2'-diol and converting the MOM ether of 5,5'-diallylbiphenyl-2,2-diol with trimethylsilane chloride (TMS-Cl) in methanol to obtain -magnolol.

In yet another embodiment, the invention encompasses a method of producing magnolol (5,5'-diallylbiphenyl-2,2'-diol) or a derivative or analogue thereof comprising converting MOM ether of 5,5'-diallylbiphenyl-2,2'-diol or a derivative or analogue thereof in an organic solvent with a suitable agent to obtain magnolol or a derivative or analogue thereof.

In yet another embodiment, the invention encompasses a method of producing magnolol (5,5'-diallylbiphenyl-2,2'-diol) comprising converting MOM ether of 5,5'-diallylbiphenyl-2,2'-diol in methanol with trimethisilane chloride to obtain magnolol. In another embodiment, the invention encompasses a composition comprising an orally or pharmaceutically acceptable carrier, and an effective amount of magnolol or a derivative or analogue thereof produced according to any of the methods described herein, in another embodiment, the invention encompasses a composition comprising an orally or pharmaceutically acceptable carrier, and an effective amount of magnolol produced according to any of the methods described herein.

Specific Embodiments of the Invention

The following examples illustrate specific embodiments of the method for producing magnolol or a derivative or analogue thereof.

Preparation of 5,5'-dibromo-2,2'-bisphenol (Formula III)

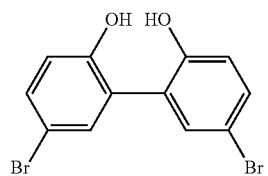

III

To a stirred solution of 2,2'-bisphenol (1.0 g, 5.3 mmol) in chloroform (20 mL) was added slowly a solution of bromine (1.97 mL, 16.1 mmol) in chloroform (10 mL) in dropwise manner at room temperature. Alter 2 h, the reaction mixture was quenched with 10% sodium bisulphite and then extracted with ethyl acetate (2×50 mL). The combined extracts were washed with brine, dried over anhydrous Na₂SO₄ and concentrated under reduced pressure. The resulting crude residue was purified by flash column chromatography to give 5,5'-dibromo-2,2'-bisphenol in 1.72 g, (93% yield) as a white solid, m.p. 186-189° c Preparation of MOM ether of 5,5'-dibromo-2,2'-bisphenol (Formula IV)

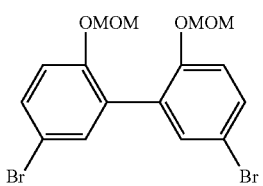

IV

A solution of 5,5'-dibromo-2,2'-bisphenol (1.0 g, 2.9 mmol) in dry dichloromethane was added diisopropylethyl amine (7.3 ml, 21.5 mmol) at 0° C. The resulting solution was stirred over 30 min and then MOM-Cl was added (1.7 mL, 10.75 mmol) at the same temperature. The mixture as allowed to stir for overnight and then quenched with water. The aqueous layer was extracted twice with dichloromethane (2×50 mL). The combined organic layers were dried over anhydrous sodium sulphate and concentrated under reduced pressure. The resulting crude product was purified by flash column chromatography to afford MOM ether in 1.19 g (95% yield) as a white solid, m.p. 120-122.

Preparation of MOM ether of 5,5'-diallylbiphenyl-2,2'-diol

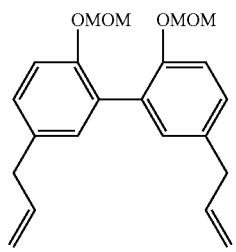

A solution of ethyl bromide (0.34 mL, 4.64 mmol) was added in portions to magnesium turnings (0.222 g, 9.3 mmol) in tetrahydrofuran (10 mL) under nitrogen atmosphere. when all the ethyl bromide (half of the magnesium present) had reacted, the reaction mixture was chilled in ice bath and a solution of MOM ether of 5,5'-dibromo-2,2'-bisphenol (1.0 g, 2.32 mmol) in dry THF (20 mL) was added slowly dropwise under nitrogen atmosphere. The resulting mixture was stirred at room temperature for 24 h and then allyl bromide (2 mL) was added slowly at 0° C. The mixture was allowed to stir for another 3 h at room temperature and then quenched with ammonium chloride solution (15 mL). The aqueous layer was extracted twice with ethyl acetate (2×50 mL). The combined organic layers were dried over anhydrous sodium sulphate and concentrated under reduced pressure. The resulting crude product was purified by flash column chromatography to give pure allyl derivative in 0.5) g, 80% yield as colourless liquid.

Preparation of MOM ether of 5,5'-di((E)-but-2-enyl)-2,2'-bis(methoxymethoxy)-biphenyl

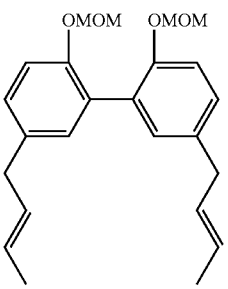

The synthesis of the MOM ether of 5,5'-di((E)-but-2-enyl) biphenyl-2,2'-diol was similarly carried out as described for the synthesis of MOM ether of magnolol, and the MOM ether of 5,5'-di((E)-but-2-enyl)biphenyl-2,2'-diol was obtained in 70% yield.

Preparation of MOM ether of 5,5'-dicinnamylbiphenyl-2,2'-diol

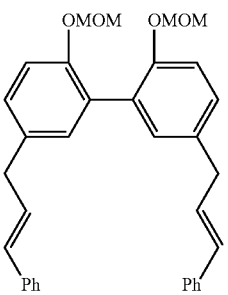

The synthesis of the MOM ether of 5,5'-dicinnamylbiphenyl-2,2'-diol was also similarly carried out as described for the synthesis of MOM ether of magnolol, and the MOM ether of 5,5'-dicinnamylbiphenyl-2,2'-diol was obtained in 72% yield.

Preparation of 5,5'-diallylbiphenyl-2,2'-diol (magnolol)

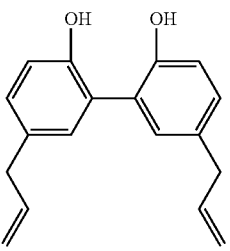 [SMILES: C=CCc1ccc(O)c(-c2cc(CC=C)ccc2O)c1]

To a stirred solution of MOM ether of 5,5'-diallyl-2,2'-bisphenol (1 g, 2.8 mmol) in methanol (10 mL and was added TMSCl (0.35 mL, 2.8 mmol) dropwise at 0° C. The resulting solution was stirred at 25° C. for 1 h. After completion, as indicated by TLC, the mixture was quenched with a solution of saturated sodium bicarbonate and extracted twice with ethyl acetate (2×50 mL). The combined organic layers were washed with brine, dried over anhydrous sodium sulfate and concentrated under reduced pressure. The resulting crude product was purified by flash column chromatography to give the pure magnolol in 0.6 g, (90% yield) as a white solid, m.p. 101-103° C.

Preparation of 5,5'-di((E)-but-2enyl)biphenyl-2,2'-diol

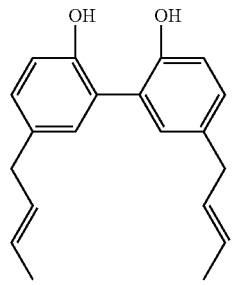 [SMILES: C/C=C/Cc1ccc(O)c(-c2cc(C/C=C/C)ccc2O)c1]

The synthesis of 5,5'-di((E)-but-2-enyl)biphenyl-2,2'-diol was also similarly carried out as described for the synthesis of magnolol, and 5,5'-di((E)-but-2-enyl)biphenyl-2,2'-diol was obtained in 91% yield.

Preparation of 5,5'-dicinnamylbiphenyl-2,2'-diol

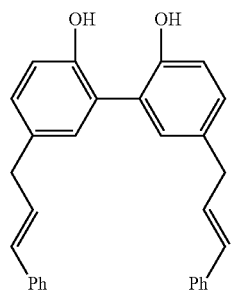 [SMILES: Oc1ccc(C/C=C/c2ccccc2)cc1-c1cc(C/C=C/c2ccccc2)ccc1O]

The synthesis of 5,5'-dicinnamylbiphenyl-2,2'-diol was also similarly carried out as described for the synthesis of magnolol, and 5,5'-dicinnamylbiphenyl-2,2'-diol was obtained in 89% yield.

The invention has been described above with reference to illustrative Examples, but it is to he understood that the invention is not limited to the disclosed embodiments. Alterations and modifications that would occur to one of Skill in the art upon reading the specification are also within the scope of the invention, which is defined in the appended claims.

We claim:

1. A method of producing a compound of formula (I)

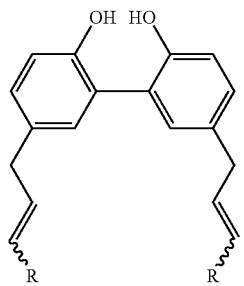

wherein R represents H, alkyl, a substituted or unsubstituted phenyl; or a pharmaceutically or orally acceptable salt thereof, comprising:

(a) reacting a compound of formula (II);

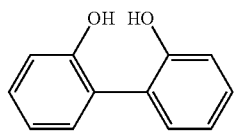

with bromine in an organic solvent to obtain a compound of formula (III);

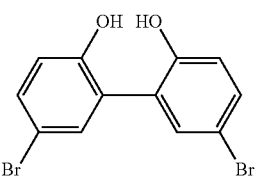

(b) reacting the compound of formula III with MOM-Cl in an organic solvent in the presence of an organic base to obtain a compound of formula (IV);

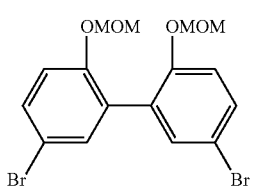

(c) reacting the compound of formula IV with R—CH═CH—CH₂—Br, wherein R is defined as above, in an organic solvent with magnesium and ethyl bromide to obtain a compound of formula V;

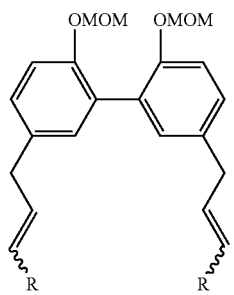

(d) converting the compound of formula V with a suitable deprotecting agent in an organic solvent to obtain a compound of formula I; and (e) optionally, converting the compound of formula I to its pharmaceutically or orally acceptable salts.

2. The method according to claim 1 wherein R is hydrogen.

3. The method according to claim 1 wherein R is methyl.

4. The method according to claim 1 wherein R is phenyl.

5. The method according to claim 1 wherein the organic solvent in (a) is chloroform.

6. The method according to claim 1 wherein the organic solvent in (c) is tetrahydrofuran.

7. The method according to claim 5 wherein the organic solvent in (c) is tetrahydrofuran.

8. The method according to claim 1 wherein the suitable deprotecting agent in (d) is trimethylsilane chloride.

9. The method according to claim 7 wherein the suitable deprotecting agent in (d) is trimethylsilane chloride.

10. A method of producing magnolol (5,5'-diallylbiphenyl-2,2'-diol) comprising:

(a) reacting 2,2'-bisphenol with bromine in chloroform to obtain 5,5'-dibromo-2,2'-bisphenol;

(b) reacting 5,5'-dibromo-2,2'-bisphenol with methoxymethylchloride (MOM-Cl) in dichloromethane with diisopropylethylamine to obtain MOM ether of 5,5'-dibromo-2,2'-bisphenol;

(c) reacting the said MOM ether of 5,5'-dibromo-2,2'-bisphenol with allyl bromide in tetrahydrofuran with magnesium and ethyl bromide to obtain MOM ether of 5,5'-diallylbiphenyl-2,2'-diol;

(d) converting the said MOM ether of 5,5'-diallylbiphenyl-2,2'-diol with a suitable deprotecting agent to obtain magnolol; and (e) optionally, converting magnolol to its pharmaceutically or orally acceptable salts.

11. The method according to claim 10 wherein the reaction of (c) is carried out at room temperature.

12. The method according to claim 10 wherein the suitable deprotecting agent in (d) is trimethylsilane chloride.

13. A method of producing compound of formula V,

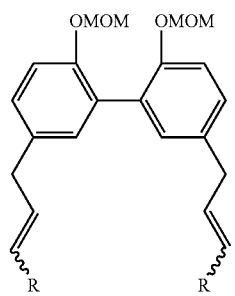

comprising reacting a compound of formula IV

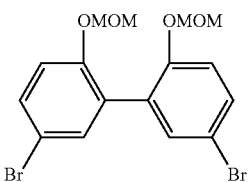

with R—CH═CH—CH₂—Br, wherein R represents H, alkyl, a substituted or unsubstituted phenyl, in an organic solvent for a sufficient amount of time to obtain a compound of formula V, and optionally converting the compound of formula V to a compound of formula I

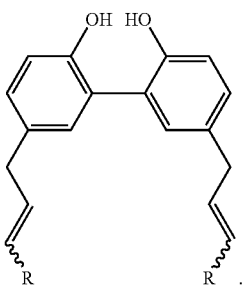

14. The method according to claim 13, wherein the organic solvent is tetrahydrofuran.

15. The method according to claim 14, wherein the reaction is carried out with magnesium and ethyl bromide to effect the coupling.

16. The method according to claim 15, wherein the reaction is carried out at room temperature.

17. The method according to claim 15, wherein the molar ratio of magnesium and ethyl bromide is about 2 to 1.

18. The method according to claim 16, wherein R is hydrogen.

19. The method according to claim 13, wherein the compound of formula V is reacted with trimethylsilane chloride in methanol to obtain a compound of formula I.

20. The method according to claim 19, wherein R is hydrogen.

* * * * *